US00PP12051P2

(12) United States Plant Patent
Cornelis

(10) Patent No.: US PP12,051 P2
(45) Date of Patent: Aug. 14, 2001

(54) SPATHIPHYLLUM PLANT NAMED 'GALAXY'

(75) Inventor: Daniel Cornelis, Merelbeke-Melsen (BE)

(73) Assignee: Milestone Agriculture, Inc., Apopka, FL (US)

( * ) Notice: Subject to any disclaimer, the term of this patent is extended or adjusted under 35 U.S.C. 154(b) by 0 days.

(21) Appl. No.: 09/592,373

(22) Filed: Jun. 12, 2000

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Spathiphyllum plant named 'Galaxy', characterized by its large, symmetrical plants; large, elongated, dark green leaves; rapid growth rate; floriferousness; large white spathes that are positioned above the foliage on strong, thick and erect peduncles; and long-lasting spathes.

2 Drawing Sheets

BACKGROUND OF THE INVENTION

The present invention relates to a new and distinct cultivar of Spathiphyllum plant, botanically known as Spathiphyllum hybrid, and hereinafter referred to by the cultivar name 'Galaxy'.

The new cultivar is a product of a planned and controlled breeding program conducted by the Inventor in Merelbeke-Melsen, Belgium. The objective of the breeding program is to create freely-flowering Spathiphyllum cultivars with large leaves and spathes. The new cultivar originated from a deliberate cross by the Inventor in 1997 of the Spathiphyllum cultivar 'Lynise', disclosed in U.S. Plant Pat. No. 6,145, as the female or seed parent and the Spathiphyllum cultivar 'Gigant', disclosed in U.S. Plant Pat. No. 7,657, as the male or pollen parent. The cultivar 'Galaxy' was discovered and selected by the Inventor as a plant within the progeny of the stated cross in a controlled environment in Merelbeke-Melsen, Belgium.

Compared to plants of the female parent, the cultivar 'Lynise', plants of the new Spathiphyllum are more symmetrical, have darker green and glossier leaves, and are more freely flowering. Compared to plants of the male parent, the cultivar 'Gigant', plants of the new Spathiphyllum have darker green leaves and larger spathes.

Asexual propagation of the new cultivar by tissue culture in a laboratory in Belgium has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity, fertilizer level and propagation procedures, without, however, any variance in genotype.

The following traits have been repeatedly observed and are determined to be the unique characteristics of 'Galaxy'. These characteristics in combination distinguish 'Galaxy' as a new and distinct cultivar:

1. Large, symmetrical plants.
2. Large, elongated, dark green leaves.
3. Rapid growth rate.
4. Very freely flowering.
5. Large white spathes that are positioned above the foliage on strong, thick and erect peduncles.
6. Long-lasting spathes.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Spathiphyllum.

The photograph on the first sheet comprises a side perspective view of a typical plant of 'Galaxy' in a 25-cm container.

The photograph on the second sheet comprises a close-view of a typical plant of 'Galaxy' in a 25-cm container.

DETAILED BOTANICAL DESCRIPTION

The following observations, measurements and comparisons describe 30-week old plants (from microcuttings) grown in Apopka, Fla., during the spring, under commercial greenhouse conditions in 25-cm containers. Day temperatures ranged from 24 to 32° C. and night temperatures ranged from 18 to 24° C. Light levels were about 1,500 foot-candles.

In the following description, color references are made to The Royal Horticultural Society Colour Chart except where general terms of ordinary dictionary significance are used.

Botanical classification: Spathiphyllum hybrid cultivar 'Galaxy'.

Parentage:

*Female parent.*—Spathiphyllum cultivar 'Lynise', disclosed in U.S. Plant Pat. No. 6,145.

*Male parent.*—Spathiphyllum cultivar 'Gigant', disclosed in U.S. Plant Pat. No. 7,657.

Propagation:

*Type.*—By tissue culture.

*Time to initiate roots.*—Summer: About 30 days at 24° C. Winter: About 45 days at 21° C.

*Time to develop roots.*—Summer: About 70 days at 24° C. Winter: About 80 days at 21° C.

*Root description.*—Freely branching, numerous fleshy roots.

Plant description:

*Plant shape.*—Upright, broad inverted triangle, symmetrical.

*Growth habit.*—Erect when young, becoming outwardly arching as leaves develop. Freely clumping with numberous new shoots; full appearance. Appropriate for 25-cm containers.

*Plant height.*—About 72 cm from soil level to top of leaf plane.

*Plant spread.*—About 102 cm.

*Plant vigor.*—Vigorous, rapid growth rate.

*Crop time.*—About 30 weeks are required to produce a finished flowering plant in 25-cm container from a tissue-cultured microcutting.

*Foliage description.*—Length: About 39 cm. Width: About 18.5 cm. Shape: Narrowly ovate. Apex: Elongated acuminate. Base: Obtuse. Margin: Entire; slightly undulate. Aspect: Initially upright, then somewhat reflexed. Surface: Rugose; midrib and lateral veins, sunken. Texture: Leathery, smooth, glabrous, very durable; flexible; both surfaces somewhat glossy. Color: Young, upper surface: Close to 147A, glossy. Young, lower surface: Slightly lighter than 147B. Mature, upper surface: Darker than 147A. Mature, lower surface: Close to 147B. Petiole: Aspect: Initally erect to about 45 to 50° to vertical with development; geniculum at leaf base, bent. Length: About 31.5 cm. Diameter, base: About 1.8 cm. Diameter, just below geniculum: About 7.5 mm. Strength: Very strong. Color: Below geniculum, 147A; geniculum, 146A. Wing length: About 26 cm. Wing width: About 1.2 cm. Geniculum length: About 4.1 cm. Geniculum diameter: About 1 cm.

Inflorescence description:

*Inflorescence arrangement.*—Concave spathes with spadices held above the foliage on strong, thick and erect peduncles. Very freely flowering; typically at least three at a time, inflorescences arise from leaf axils.

*Inflorescence longevity.*—Inflorescences are long-lasting, generally maintaining white color for about two months on the plant depending on light and temperature levels.

*Fragrance.*—Moderate, sweet, typical of Spathiphyllum.

*Spathe.*—Length: About 24 cm. Width: About 14.5 cm. Shape: Ovate. Apex: Elongated acuminate. Base: Obtuse. Aspect: Concave, curling over the spadix. Color (both surfaces): White, 155D, becoming green, close to 144A, with development. Back surface, lateral veins and apex, 146A.

*Spadix.*—Length: About 11.6 cm. Diameter: About 2.1 cm. Color: 158D becoming green, 144A, with development. Quantity of flowers: More than 300 per spadix. Pollen: White, close to 155D.

*Peduncle.*—Aspect: Very strong. Length: About 63 cm. Diameter, just below spathe: About 1 cm. Color: Towards apex, close to 144; towards base, 146A.

*Seed.*—Seed development has not been observed.

Disease resistance: Plants of the new Spathiphyllum have exhibited good resistance to pathogens common to Spathiphyllum.

Temperature tolerance: Plants of the new Spathiphyllum have been shown to tolerate temperatures from 6 to 37° C.

It is claimed:

1. A new and distinct cultivar of Spathiphyllum plant named 'Galaxy', as illustrated and described.

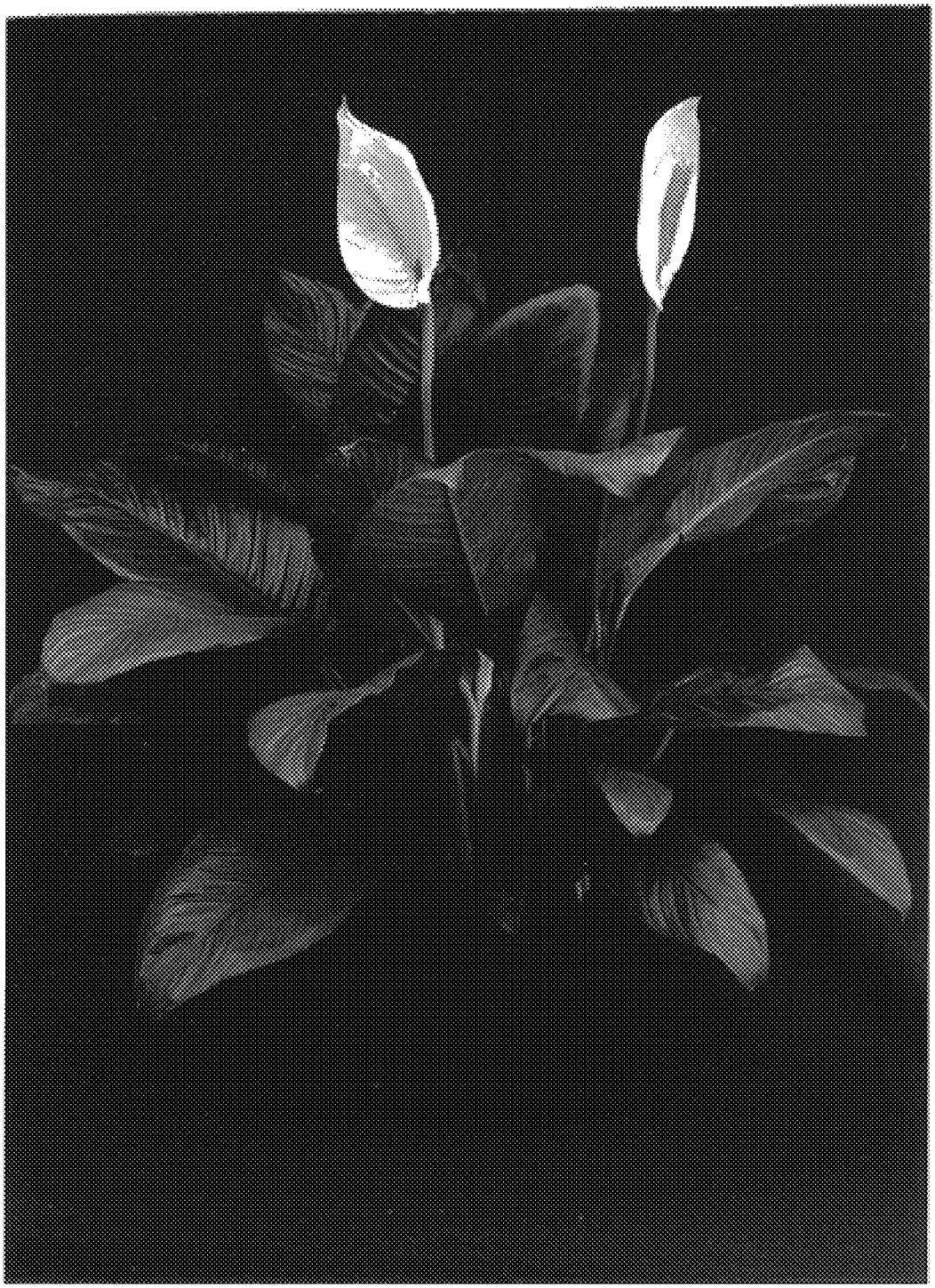

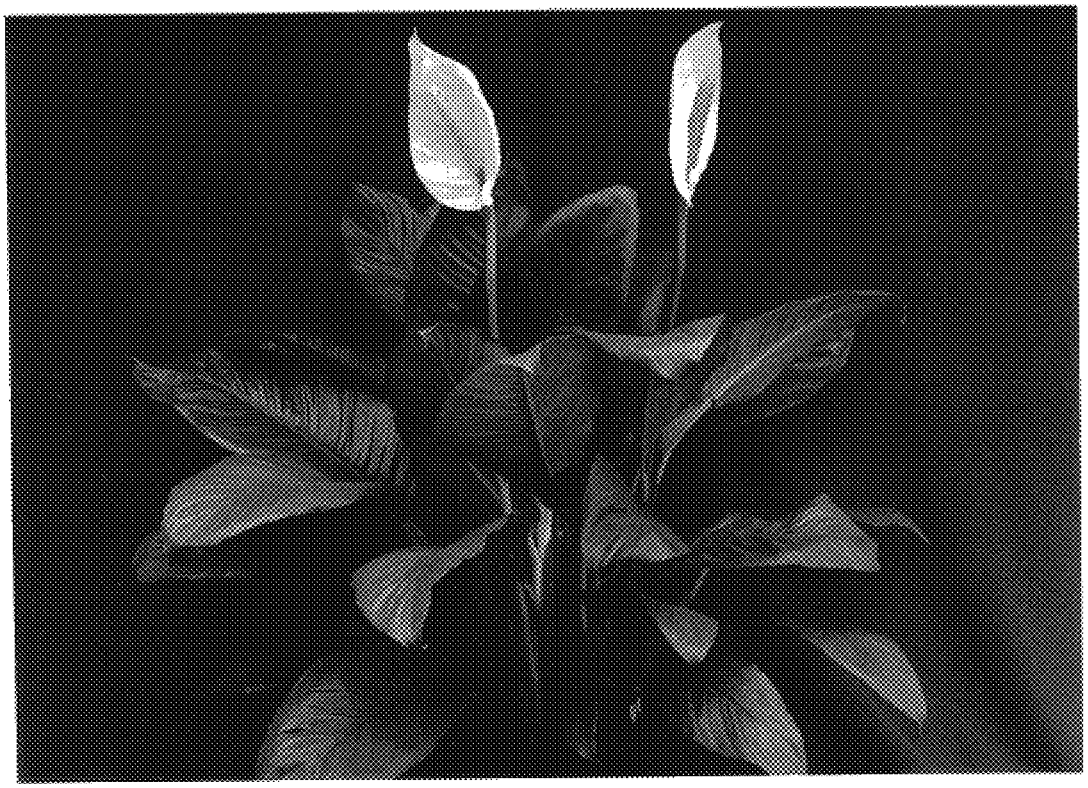

* * * * *